United States Patent [19]

Schroder et al.

[11] 3,937,712

[45] Feb. 10, 1976

[54] (5-NITRO-2-FURYL)-PYRIDINES

[75] Inventors: Ludwig Schroder, Ingelheim am Rhein; Klaus Thomas, Gau-Algesheim; Hanns Goeth, Biberach and der Riss, all of Germany

[73] Assignee: Boehringer Ingelheim GmbH, Ingelheim am Rhein, Germany

[22] Filed: May 28, 1974

[21] Appl. No.: 473,324

Related U.S. Application Data

[63] Continuation-in-part of Ser. No. 290,334, Sept. 19, 1972, Pat. No. 3,518,256.

[30] Foreign Application Priority Data

Sept. 22, 1971 Germany............................ 2147288

[52] U.S. Cl. ...... 260/296 AE; 424/263; 260/296 R; 260/297 R; 260/297 Z
[51] Int. Cl.² ........................................ C07D 213/44
[58] Field of Search...... 260/296 AB, 296 R, 297 Z, 260/297 R

[56] References Cited
UNITED STATES PATENTS

| | | | |
|---|---|---|---|
| 3,518,256 | 6/1970 | Minami et al. | 260/240 A |
| 3,666,765 | 5/1972 | Berijckere et al. | 260/290 HL |
| 3,829,426 | 8/1974 | Schroder et al. | 260/297 Z |

OTHER PUBLICATIONS

Miura et al., Progress in Medicinal Chemistry, Vol. 5, Chapter 6, pp. 320 to 337, Butterworths, London, England (1967).

*Primary Examiner*—John D. Randolph
*Attorney, Agent, or Firm*—Hammond & Littell

[57] ABSTRACT

Compounds of the formula

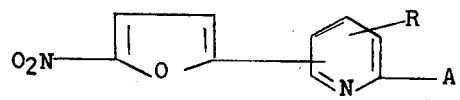

wherein
  A is chlorine, alkoxy of 1 to 10 carbon atoms, dimethylamino-ethoxy or diethylamino-ethoxy, and
  R is hydrogen, alkyl of 1 to 4 carbon atoms or pyridyl;
the compounds are useful as antimicrobial agents, especially against gramnegative microorganisms, for the treatment of infections of the intestinal and urogential tract.

6 Claims, No Drawings

(5-NITRO-2-FURYL)-PYRIDINES

This is a continuation-in-part of copending application Ser. No. 290,334, filed Sept. 19, 1972, now U.S. Pat. No. 3,518,256.

This invention relates to novel (5-nitro-2-furyl)pyridines, as well as to a method of preparing these compounds.

More particularly, the present invention relates to a novel class of nitrofuryl-substituted pyridines of the formula

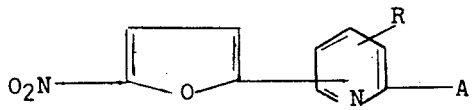

wherein
A is chlorine, alkoxy of 1 to 10 carbon atoms, dimethylamino-ethoxy or diethylamino-ethoxy, and
R is hydrogen, alkyl of 1 to 4 carbon atoms or pyridyl.

A particularly preferred subgenus of the compounds according to the present invention are those of the formula

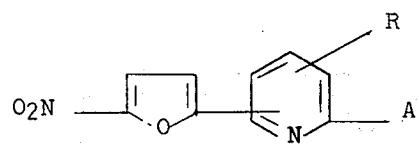

wherein
A is chlorine, methoxy, n-propoxy, n-butoxy, n-decyloxy, dimethylamino-ethoxy or diethylamino-ethoxy, and
R is hydrogen, methyl or pyridyl.

The compounds embraced by formula I may be prepared by nitrating a 2-furyl-pyridine of the formula

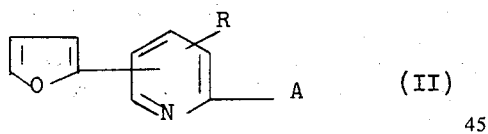

wherein R and A have the same meanings as in formula I, pursuant to conventional methods, such as by reaction with a mixture of concentrated nitric acid and concentrated sulfuric acid at a temperature between −20° and +20°C.

The starting compounds of the formula II, in turn, may be prepared by the following methods:

Method A

By first preparing an α,β-unsaturated ketone of the formula

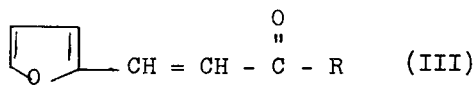

wherein R has the same meanings as in formula I, pursuant or analogous to the procedure described in Arch. Pharm. 297 (1964), 42 et seq., and subjecting said ketone to a condensation reaction with a pyridinium salt of the formula

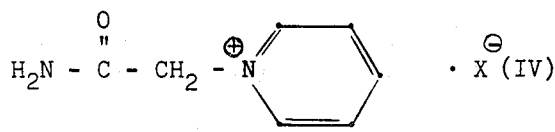

wherein X is halogen, preferably chlorine, pursuant or analogous to the procedure described in Chem. Ber. 90 (1957), 711, whereby a compound of the formula

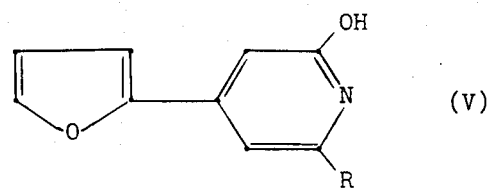

wherein R has the meanings defined in connection with formula I, is obtained.

Method B

By reacting an α,β-unsaturated keton of the formula III with a pyridinium salt of the formula

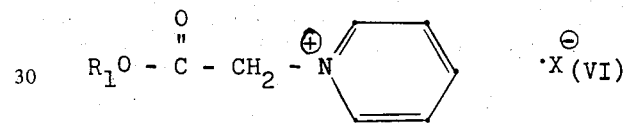

wherein $R_1$ is methyl or ethyl and X is halogen, preferably chlorine, in the presence of ammonium acetate and of a suitable solvent medium, preferably glacial acetic acid or ethanol, pursuant or analogous to the procedure described in Chem. Ber. 103 (1970), 322, whereby a compound of the formula V is also formed.

Method C

By reacting a Mannich base of the formula

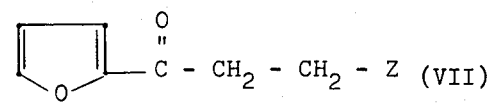

wherein Z is secondary amine, such as dimethylamino or piperidino, or a salt thereof, with a pyridinium salt of the formula VI under the conditions set forth in method B, whereby the compound of the formula

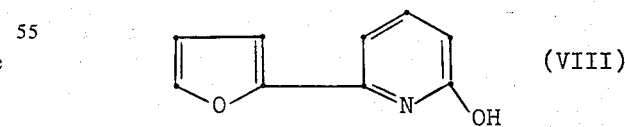

is obtained.

Method D

By subjecting 2-acetyl-furan to a condensation reaction with a pyridyl-aldehyde (see German Offenlegungsschrift 2,001,819) in the presence of perchloric acid to form a ketone of the formula

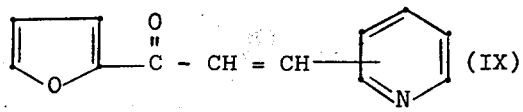 (IX)

which may then be cyclized pursuant to method A or B with a pyridinium salt of the formula IV or VI to yield a compound of the formula

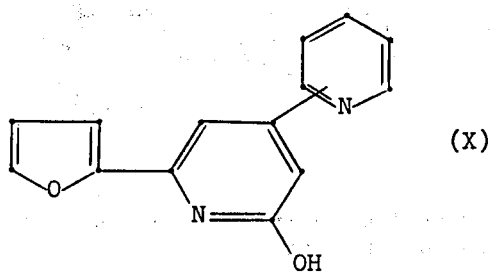 (X)

Method E

By subjecting 2-acetyl-furan to a condensation reaction with an aliphatic or aromatic aldehyde (with the exception of a pyridyl-aldehyde referred to in method D) to form an α,β-unsaturated ketone of the formula

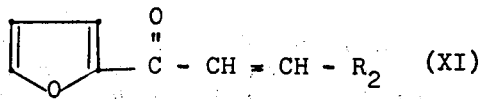 (XI)

wherein $R_2$ has the meanings defined for R in formula I except hydrogen, 2-pyridyl, 3-pyridyl and 4-pyridyl, wich may then be cyclized with a pyridinium salt of the formula IV or VI to yield a compound of the formula

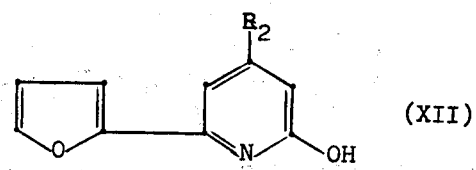 (XII)

wherein $R_2$ has the meanings defined above.

Method F

The compounds of the formula II wherein A is hydroxyl exist in tautomeric equilibrium with the corresponding pyridones

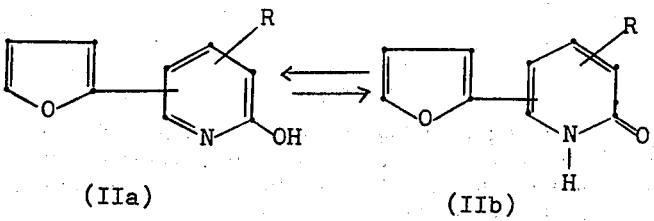

and such a tautomeric mixture may be reacted with a conventional chlorinating agent, preferably phosphorus oxychloride ($POCl_3$), at elevated temperatures, preferably between 100° and 180°C., under pressure to yield a compound of the formula

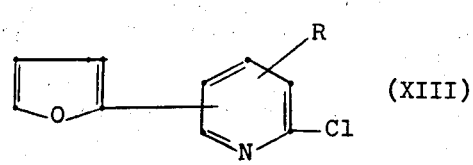 (XIII)

wherein R has the same meanings as in formula I.

Method G

For the preparation of a compound of the formula

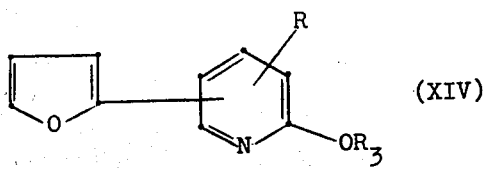 (XIV)

wherein R has the same meanings as in formula I and $R_3$ is alkyl of 1 to 10 carbon atoms, dimethylamino-ethyl or diethylamino-ethyl, by reacting a compound of the formula XIII with an alkali metal alcoholate, preferably with a sodium alcoholate of the formula

$R_3 ONa$ (XV)

wherein $R_3$ has the meanings defined above, advantageously in a suitable solvent medium at elevated temperatures, preferably between 80° and 200°C. Examples of suitable solvent media are, in addition to an excess of an alcohol of the formula $R_3OH$, where $R_3$ has the meanings previously defined, also inert solvents, such as acetonitrile, toluene, dimethylformaide or dioxane.

The following examples further illustrate the present invention and will enable others skilled in the art to understand it more completely. It should be understood, however, that the invention is not limited solely to the particular examples given below.

EXAMPLE 1

2-(β-Dimethylamino-ethoxy)-6-(5′-nitro-2′-furyl)-pyridine a. (β-Dimethylamino-ethyl)-(furyl-2)keton hydrochloride 440 gm (4 mols) of 2-acetyl-furan, 240 gm (8 mols) of paraformaldehyde and 406 gm (5 mols) of dimethylamine hydrochloride were suspended in 960 ml of ethanol, 10 ml of concentrated hydrochloric acid were added to the suspension, and the resulting mixture was boiled for four hours, accompained by stirring. Thereafter, the reaction mixture was allowed to cool, and the crystalline precipitate was collected by vacuum filtration, yielding 73% of theory of the Mannich salt of the formula

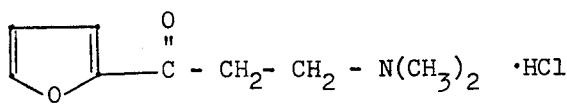

which had a melding point of 180° – 181°C.

b. 6-(Furyl-2')-2(1H)-pyridone by method B 43.5 gm (0,55 mol) of pyridine were heated to 100°C., and then 61 gm (0.5 mol) of ethyl chloroacetate were added dropwise at a rate such that the temperature of the mixture was held at 105°C. without exterior heating. After all of the chloroacetate had been added and the reaction had subsided, the molten mixture was taken up in 300 ml of ethanol, 0.5 mol of the Mannich salt obtained in (a) and 300 gm of ammonium acetate were added to the solution, and the mixture was refluxed for 2.5 hours. Thereafter, the ethanol was distilled off in vacuo, the residue was triturated with about 200 ml of water, and the crystalline product was collected by vacuum filtration and recrystallized from isopropanol, yielding 56% of theory of the compound of the tautomeric formulas

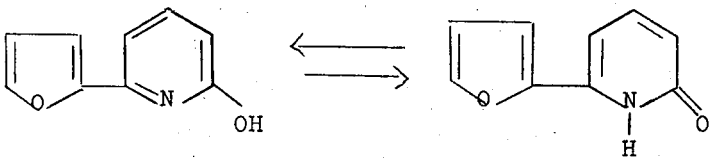

which had a melting point of 168° – 169°C.

c. 2-(β-Dimethylamino-ethoxy)-6-(furyl-2')pyridine by method D

A mixture consisting of 8.05 gm (0.05 mol) of the end product of (b), 10.5 gm of potassium carbonate and 80 ml of dimethylformamide was heated to 120° – 130°C., and then, while stirring, a total of 8.6 gm (0.06 mol) of 2-dimethylamino-ethyl chloride hydrochloride were added in small portions over a period of about two hours. The resulting mixture was stirred for five hours more at 120° – 130°C. and was then poured into 300 ml of water, and the aqueous phase was separated and extracted with ether. The ethereal extract was dried over potassium carbonate, evaporated, and the residue was distilled in vacuo, yielding the compound of the formula

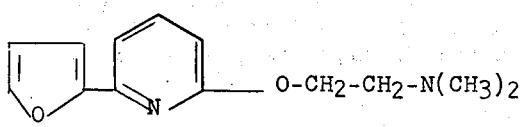

which had a b.p. of 107°–108°C. at 0.05 mm Hg.

d. The end product obtained in (c) was nitrated in the following manner. 2 mols of this end product were introduced into 1.5 liters of concentrated sulfuric acid at 40° – 50°C., while stirring. The resulting mixture was cooled at 0°C., and then a mixture consisting of 100 ml of concentrated nitric acid ($d = 1.53$; 2.4 mols) and 200 ml of concentrated sulfuric acid was added dropwise thereto over a period of 2 hours. The nitration reaction mixture was poured into water, and the resulting clear solution was neutralized with ammonia. The resulting aqueous solution was extracted with ether, the ethereal extract was dried and evaporated and the residue was taken up in gasoline and caused to crystallize therefrom by deep cooling. The compound of the formula

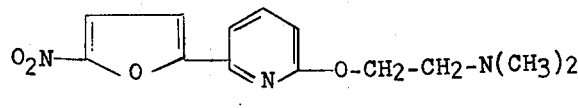

with a melting point of 42° – 44°C was obtained

EXAMPLE 2

2-(Pyridyl-2')-4-(5''-nitro-2''-furyl)-6-chloro-pyridine a. 1-(Furyl-2')-3-(pyridyl-2'')-propen-(1)-one-(3)

4 liters of 1N sodium hydroxide were cooled to 0°C. in a vessel having a capacity of 10 liters, and then, while stirring, a mixture consisting of 605 gm (5 mols) of 2-acetyl-pyridine and 480 gm (5 mols) of 2-furaldehyde was allowed to flow into the vessel over a period of one hour. Thereafter, the reaction mixture was stirred for one hour more at 0°C., then vacuum-filtered, and the filter cake was washed with 10 liters of water, dried and recrystallized from benzene/cyclohexane, yielding 96.5% of theory of the ketone of the formula

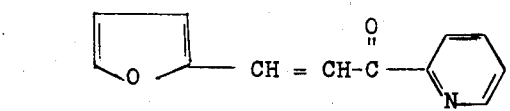

which had a melting point of 50° – 51°C.

b. 2-(Pyridyl-2')-4-(furyl-2'')-pyridone-(6) by Method B

A mixture consisting of 800 gm (4 mols) of the ketone obtained in (a), 965 gm (4.8 mols) of carbethoxymethyl-pyridinium chloride, 2.4 kg of ammonium acetate and 2.5 liters of ethanol was refluxed for one hour. Thereafter the still hot reaction solution was poured into 8 liters of water, and the precipitate formed thereby was collected by vacuum filtration and recrystallized from ethanol, yielding 89% of theory of the compound of the tautomeric formulas

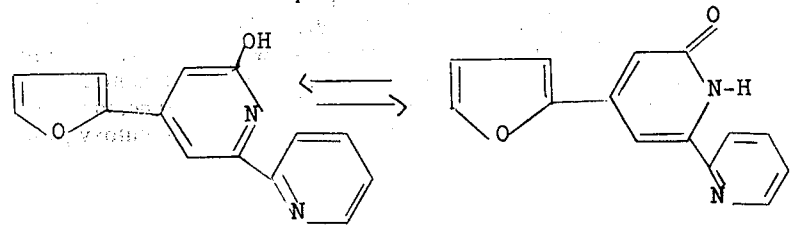

which had a melting point of 207° – 208°C.

c. 2-(Pyridyl-2')-4-(furyl-2'')-6-chloropyridine by method C

A mixture consisting of 23.8 gm (0.1 mol) of the end product of (b) and 50 ml of phosphorus oxychloride was heated for 5 hours at 150°C in a closed tube. Thereafter, the reaction mixture was introduced into ice water, and the aqueous mixture was neutralized with sodium hydroxide. The crystalline precipitate formed thereby was collected by vacuum filtration and recrystallized from isopropanol, yielding the compound of the formula

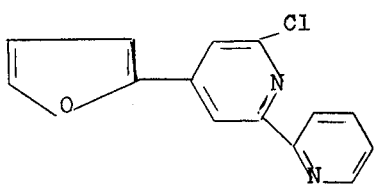

which had a melting point of 168°–170°C.

d. 2 mols of the end product obtained in (c) were introduced into 1.5 liters of concentrated sulfuric acid at 40° – 50°C., while stirring. The resulting mixture was cooled to 0°C., and then a mixture consisting of 100 ml of concentrated nitric acid ($d$ = 1.53; 2.4 mols) and 200 ml of concentrated sulfuric acid was added dropwise thereto over a period of two hours. The resulting dark solution was then poured into 8 liters of water, the precipitate formed thereby was collected by vacuum filtration and again suspended in about 8 liters of water, and the aqueous suspension was admixed with ammonium hydroxide until it reacted distinctly alkaline. The alkaline aqueous mixture was again vacuum-filtered, and the filter cake was washed with an ample amount of water and recrystallized from glacial acetic acid, yielding the compound of the formula

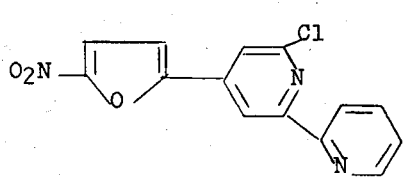

having a melting point of 174°–175°C.

EXAMPLE 3

2-(Pyridyl-2')-4-(5''-nitro-2''-furyl)-6-methoxy-pyridine.

a. 2-(Pyridyl-2')-4-(furyl-2'')-6-methoxy-pyridine by method D

A mixture consisting of 10 gm (0.04 mol) of the end product of Example 2(c), 5.5 gm (0.1 mols) of sodium methylate and 100 ml of methanol was heated for 5 hours at 150°C in a pressure vessel. Thereafter, the reaction solution was evaporated, the residue was taken up in water, the aqueous mixture was vacuum-filtered, and the filter cake was recrystallized from cyclohexane, yielding the compound of the formula

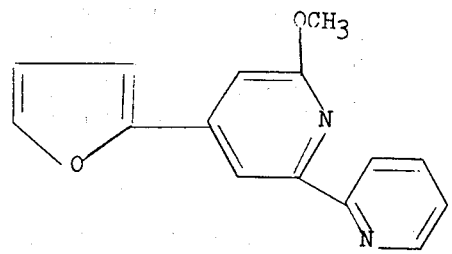

which had a melting point of 124°C.

b. Using a procedure analogous to that described in Example 2 (d), the compound of the formula

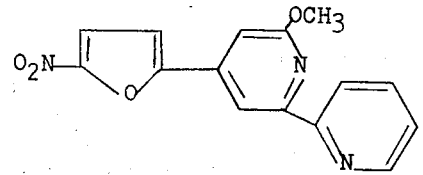

having a melting point of 209°–210°C was obtained from the end product of (a).

EXAMPLE 4

Using a procedure analogous to that described in Example 2 (d), 2-(5'-nitro-2'-furyl)-4-(pyridyl-4'')-6-chloropyridine, m.p. 249°–250°C, of the formula

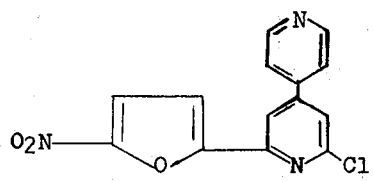

was obtained from 2-(furyl-2')-4-(pyridine-4'')-6-chloro pyridine.

EXAMPLE 5

Using a procedure analogous to that described in Example 2 (d), 2-(5'-nitro-2'-furyl)-6-methoxy-pyridine, m.p. 136°–138°C, of the formula

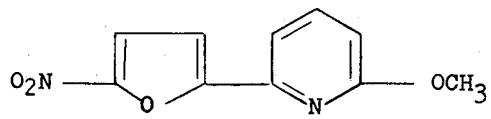

was obtained from 2-(furyl-2')-6-methoxy-pyridine.

EXAMPLE 6

Using a procedure analogous to that described in Example 2 (d), 2-(5'-nitro-2'-furyl)-6-n-decyloxy-pyridine, m.p. 40°–41°C, was obtained from 2-(furyl-2')-6-n-decyloxy-pyridine.

EXAMPLE 7

Using a procedure analogous to that described in Example 2 (d), 2-(5'-nitro-2'-furyl-6-n-butoxy-pyridine, m.p. 58°–60°C, was obtained from 2-(furyl-2')-6-n-butoxy-pyridine.

EXAMPLE 8

Using a procedure analogous to that described in Example 2 (d), 2-(pyridyl-4′)-4-(5′′′-nitro-2′′-furyl)-6-methoxy-pyridine, m.p. 158°–160°C, of the formula

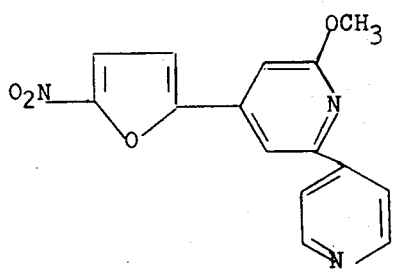

was obtained from 2-(pyridyl-4′)-4-(furyl-2′′)-6-methoxy-pyridine.

EXAMPLE 9

Using a procedure analogous to that described in Example 2 (d), 2-(pyridyl-3′)-4-(5′′′-nitro-2′′-furyl)-6-methoxy-pyridine, m.p. 168°–171°C, was obtained from 2-(pyridyl-3′)-4-(furyl-2′′)-6-methoxy-pyridine.

EXAMPLE 10

Using a procedure analogous to that described in Example 2 (d), 2-methyl-4-(5′-nitro-2′-furyl)-6-methoxy-pyridine, m.p. 230°–231°C, of the formula

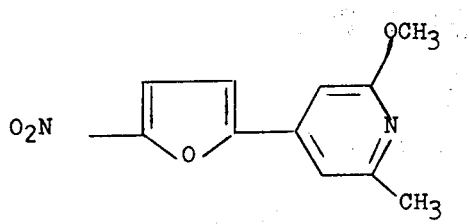

was obtained from 2-methyl-4-(furyl-2′)-6-methoxy-pyridine.

EXAMPLE 11

Using a procedure analogous to that described in Example 2 (d), 2-methyl-4-(5′-nitro-2′-furyl)-6-n-propoxy-pyridine, m.p. 95°–100°C, was obtained from 2-methyl-4-(furyl-2′)-6-n-propoxy-pyridine.

EXAMPLE 12

Using a procedure analogous to that described in Example 2 (d), 2-methyl-4-(5′-nitro-2′-furyl)-6-(β-diethylamino-ethoxy)-pyridine, m.p. 78°–79°C, of the formula

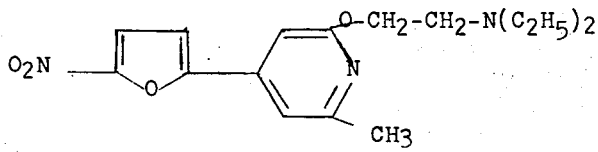

was obtained from 2-methyl-4-(furyl-2′)-6-(β-diethylamino-ethoxy)-pyridine.

EXAMPLE 13

Using a procedure analogous to that described in Example 2 (d), 2-methyl-4-(5′-nitro-2′-furyl)-6-n-decyloxy-pyridine, m.p. 52°–54°C, was obtained from 2-methyl-4-(furyl-2′)-6-n-decyloxy-pyridine.

EXAMPLE 14

Using a procedure analogous to that described in Example 2 (d), 2-chloro-4-(pyridyl-2′)-6-(5′′-nitro-2′′-furyl)-pyridine, m.p. 214°–216°C, was obtained from 2-chloro-4-(pyridyl-2′)-6-(furyl-2′′)-pyridine.

EXAMPLE 15

Using a procedure analogous to that described in Example 2 (d), 2-chloro-4-(pyridyl-3′)-6-(5′′-nitro-2′′-furyl)-pyridine, m.p. 228°–229°C, was obtained from 2-chloro-4-(pyridyl-3′)-6-(furyl-2′′)-pyridine.

EXAMPLE 16

Using a procedure analogous to that described in Example 2 (d), 2-methoxy-4-(pyridyl-3′)-6-(5′′-nitro-2′′-furyl)-pyridine, m.p. 187°–188°C, was obtained from 2-methoxy-4-(pyridyl-3′)-6-(furyl-2′′)-pyridine.

The compounds embraced by formula I have useful pharmacodynamic properties. More particularly, they exhibit antimicrobial activity against a broad spectrum of pathogenic bacteria, fungi and protozoa, such as *Staph. aureus*, Streptoc.; *E. coli*, Salmonellen, Shigellen, *Klebsilla pneum.*; *Trich. ment.*; *Trichomonas vag.*, *Trichomonas foet.*; *Entamoeba hist.*, especially against gramnegative microorganisms, coupled with low toxicity, and may therefore be effectively used externally as well as internally, particularly for combatting infections of the intestinal and urogenital tract in warm-blooded animals, such as dogs, cats, horses and cattle.

Especially well suited for external use are those compounds of the formula I wherein R is alkyl, particularly methyl; for internal use, those wherein R is pyridyl are especially well suited.

For pharmaceutical purposes the compounds according to the present invention are administered to warm-blooded animals topically, perorally or parenterally as active ingredients in customary pharmaceutical compositions, that is, compositions consisting essentially of an inert pharmaceutical carrier and effective amount of the active ingredient, such as tablets, coated pills, capsules, wafers, powders solutions, suspensions, emulsions, syrups, suppositories, ointments, tinctures and the like. An effective amount of the compounds according to the present invention for internal administration is from 1.0 to 100.0 mgm/kg body weight; their effective concentration in compositions for external application is from 0.1 to 10.0% by weight based on the total weight.

The following examples illustrate a few pharmaceutical compositions comprising a compound of the present invention as an active ingredient and represent the best modes contemplated of putting the invention into practical use. The parts are parts by weight unless otherwise specified.

EXAMPLE 17

Tablets

The tablet composition is compounded from the following ingredients:

| | | |
|---|---:|---|
| 2-(β-Dimethylamino-ethoxy)-6-(5′-nitro-2′-furyl)-pyridine | 100.0 | parts |
| Corn starch | 125.0 | " |
| Lactose | 85.0 | " |
| Colloidal silicic acid | 5.0 | " |
| Soluble starch | 8.0 | " |
| Magnesium stearate | 2.0 | " |
| Total | 325.0 | parts |

Preparation:

The pyridine compound, the lactose and 110 parts of the corn starch are intimately admixed with each other, the mixture is granulated through a screen with the aid of an aqueous solution of the soluble starch, the dried granulate is admixed with the remaining ingredients, and the resulting composition is compressed into 325 mgm-tablets in a conventional tablet-making machine. Each tablet contains 100 mgm of the pyridine compound and is an oral dosage unit composition with effective antimicrobial action.

EXAMPLE 18

Coated pills

The pill core composition is compounded from the following ingredients:

| | | |
|---|---:|---|
| 2-(Pyridyl-2')-4-(5''-nitro-2'' furyl)-6-chloro-pyridine | 100.0 | parts |
| Lactose | 50.0 | '' |
| Corn starch | 60.0 | '' |
| Colloidal silicic acid | 3.0 | '' |
| Soluble starch | 5.0 | '' |
| Magnesium stearate | 2.0 | '' |
| Total | 220.0 | parts |

Preparation:

The pyridine compound, the lactose and 50 parts of the corn starch are initimately admixed with each other, the mixture is granulated through a screen with the aid of an aqueous solution of the soluble starch, the dried granulate is admixed with the remaining ingredients, and the resulting composition is compressed into 220 mgm-pill cores which are subsequently coated with a thin shell consisting essentially of a mixture of sugar, talcum, gum arabic and titanium dioxide. Each coated pill contains 100 mgm of the pyridine compound and is an oral dosage unit composition with effective antimicrobial action.

EXAMPLE 19

Suspension

The suspension is compounded from the following ingredients:

| | | |
|---|---:|---|
| 2-(Pyridyl-2')-4-(5''-nitro-2''-furyl) -6-methoxy-pyridine | 5.0 | parts |
| Saccharose | 20.0 | parts |
| Sodium carboxymethyl cellulose | 2.0 | parts |
| Glycerin | 5.0 | '' |
| Flavoring | q.s. | |
| Preservative | q.s. | |
| Demineralized water    q.s.ad | 100.0 | '' |

Preparation:

The ground mixture of the pyridine compound, the sodium carboxymethyl cellulose and the glycerin is stirred into the solution of the saccharose and the preservative in the demineralized water, the cellulose was allowed to swell, and then the flavoring is added and the composition is homogenized. The resulting aqueous suspension is an oral dosage unit composition with effective antimicrobial action.

EXAMPLE 20

Lozenges

The lozenge composition is compounded from the following ingredients:

| | | |
|---|---:|---|
| 2-(5'-Nitro-2'-furyl)-4-(pyridyl -4'')-6-chloro-pyridine | 5.0 | parts |
| Glucose monohydrate | 380.0 | '' |
| Saccharose, powdered | 200.0 | '' |
| Stearic acid | 15.0 | '' |
| Total | 600.0 | parts |

Preparation:

The pyridine compound, the glucose and the saccharose are admixed with each other, the mixture is granulated through a screen with a solution of the stearic acid in 60 gm of ethanol, and the dried granulate is compressed into 600 mgm-lozenges. Each lozenge contains 5 mgm of the pyridine compound and is an oral dosage unit composition with effective antimicrobial action.

EXAMPLE 21

Tincture

The tincture composition is compounded from the following ingredients:

| | | |
|---|---:|---|
| 4-(5'-Nitro-2'-furyl)-6-methyl-2 -($\beta$-diethylamino-ethoxy)-pyridine | 2.0 | parts |
| Ethanol | 70.0 | '' |
| Glycerin | 10.0 | '' |
| Cremophor EL | 2.0 | '' |
| Perfume | q.s. | |
| Demineralized water    q.s.ad | 100.0 | '' |

Preparation:

The prefume, the Cremophor and the pyridine compound are dissolved in the ethanol, and then the mixture of glycerin and demineralized water is slowly stirred into the ethanolic solution. The resulting tincture is a topical composition with effective antimicrobial action.

EXAMPLE 22

Ointment

The ointment composition is compounded from the following ingredients:

| | | |
|---|---:|---|
| 4-(5'-Nitro-2'-furyl)-6-methyl-2 -($\beta$-diethylamino-ethoxy)-pyridine | 2.0 | parts |
| Vaseline | 35.0 | '' |
| Paraffin oil | 12.0 | '' |
| Ceresin | 5.0 | '' |
| Cremophor FM new | 3.0 | '' |
| Wool grease | 4.0 | '' |
| Preservative | q.s. | |
| Perfume | q.s. | |
| Demineralized water    q.s.ad | 100.0 | '' |

Preparation:

The vaseline, the ceresin, the Cremophor and the wool grease are intimately admixed with each other, the mixture is heated to 70°C, and then a mixture of the finely divided pyridine compound with the paraffin oil is stirred in. Subsequently, a solution of the preservative in the demineralized water at 70°C is added, the resulting mixture is homogenized, the perfume is added, and the finished composition is stirred until it has cooled. The resulting ointment is a topical composition with effective antimicrobial action.

EXAMPLE 23

Cream

The cream is compounded from the following ingredients:

| | | |
|---|---|---|
| 4-(5'-Nitro-2'-furyl)-6-methyl-2-(β-diethylamino-ethoxy)-pyridine | 2.0 | parts |
| Stearyl alcohol | 10.0 | " |
| Yellow vaseline | 15.0 | " |
| Yellow wax | 5.0 | " |
| Glycerin monostearate | 3.0 | " |
| Spermaceti | 5.0 | " |
| Cremophor O | 1.0 | " |
| Glycerin | 10.0 | " |
| Preservative | q.s. | |
| Perfume | q.s. | |
| Demineralized water q.s.ad | 100.0 | " |

Preparation:

The finely divided pyridine compound, the yellow vaseline, the yellow wax, the stearyl alcohol, the glycerin monostearate, the spermaceti and the Cremophor are intimately admixed with each other, and the mixture is heated to 70°C. A solution of the preservative in the mixture of the glycerin and water at 70°C is then added, the composition is homogenized, the prefume is added, and the finished cream is stirred until it has cooled. The cream is a topical composition with effective antimicrobial action.

EXAMPLE 24

Powder

The powder is compounded from the following ingredients:

| | | |
|---|---|---|
| 2-(5'-Nitro-2'-furyl)-6-methoxy-pyridine | 2.0 | parts |
| Perfume | q.s. | |
| Colloidal silicic acid | 3.0 | " |
| Talcum | 40.0 | " |
| Wheat starch q.s.ad | 100.0 | " |

Preparation:

The ingredients are admixed, and the mixture is milled into a powder which is a topical composition with effective antimicrobial action.

Analogous results are obtained when any one of the other pyridine derivatives embraced by formula I is substituted for the particular pyridine compound in Examples 17 through 24. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

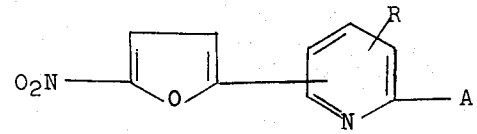

wherein
A is alkoxy of 1 to 10 carbon atoms, dimethylamino-ethoxy or diethylamino-ethoxy, and
R is hydrogen, alkyl of 1 to 4 carbon atoms, or pyridyl.

2. A compound of claim 1 wherein A has the meanings defined in claim 1 and R is alkyl of 1 to 4 carbon atoms.

3. A compound of claim 1 wherein A has the meanings defined in claim 1 and R is methyl.

4. A compound of claim 1 wherein A has the meanings defined in claim 1 and R is pyridyl.

5. The compound of claim 1 which is 4-(5'-nitro-2'-furyl)-6-methyl-2-(β-diethylamino-ethoxy)-pyridine.

6. A compound of claim 1, wherein A is methoxy, n-propoxy, n-butoxy, n-decyloxy, dimethylamino-ethoxy or diethylamino-ethoxy, and R is hydrogen, methyl or pyridyl.

* * * * *